United States Patent [19]

Shah et al.

[11] Patent Number: 4,575,376

[45] Date of Patent: Mar. 11, 1986

[54] METHOD FOR INCREASING THE ABSORBENCY OF CELLULOSIC FIBERS

[75] Inventors: Shailesh Shah, Paramus; David R. King, Roxbury; Nathan D. Field, Wyckoff, all of N.J.

[73] Assignee: International Playtex, Inc. Stamford, Conn.

[21] Appl. No.: 549,356

[22] Filed: Nov. 7, 1983

[51] Int. Cl.$^4$ ............................................. D06M 1/00
[52] U.S. Cl. ..................... 8/116.1; 264/103; 264/191; 264/196; 264/198; 264/233; 264/343; 604/375; 604/904
[58] Field of Search ............... 204/233, 198, 343, 196; 8/116 R

[56] References Cited

U.S. PATENT DOCUMENTS

| | | | |
|---|---|---|---|
| 3,133,137 | 5/1964 | Loeb et al. | 264/233 |
| 3,241,553 | 3/1966 | Steiger | 128/156 |
| 3,494,995 | 2/1970 | Rainer et al. | 264/196 |
| 3,529,052 | 9/1970 | Carney et al. | 264/233 |
| 3,618,607 | 11/1971 | Ells | 128/285 |
| 3,718,722 | 2/1973 | Lee | 264/233 |
| 3,731,686 | 5/1973 | Chatterjee | 128/285 |
| 3,844,287 | 10/1974 | Smith | 128/285 |
| 3,858,585 | 1/1975 | Chatterjee | 128/290 R |
| 3,929,946 | 12/1975 | Orito et al. | 264/343 |
| 3,971,379 | 7/1976 | Chatterjee | 128/285 |
| 3,983,095 | 9/1976 | Bashaw et al. | 264/347 |
| 3,993,616 | 11/1976 | Gross | 260/29.4 UA |
| 4,017,653 | 4/1977 | Gross | 427/385 A |
| 4,041,121 | 8/1977 | Smith | 264/198 |
| 4,044,766 | 8/1977 | Kaczmarzyk et al. | 128/285 |
| 4,061,846 | 12/1977 | Gross et al. | 526/16 |
| 4,066,584 | 1/1978 | Allen et al. | 260/17.4 CL |
| 4,104,214 | 8/1978 | Meierhoefer | 264/198 |
| 4,136,697 | 1/1979 | Smith | 128/285 |
| 4,165,743 | 8/1979 | Denning | 128/290 R |
| 4,177,236 | 12/1979 | Franks | 264/198 |
| 4,240,937 | 12/1980 | Allen | 260/17.4 CL |
| 4,242,242 | 12/1980 | Allen | 260/17.4 CL |
| 4,273,118 | 6/1981 | Smith | 264/233 |
| 4,289,824 | 9/1981 | Smith | 428/288 |
| 4,399,255 | 8/1983 | Smith et al. | 264/198 |

*Primary Examiner*—Jeffery Thurlow
*Assistant Examiner*—Patrick Dailey
*Attorney, Agent, or Firm*—Stewart J. Fried; Charles N. J. Ruggiero

[57] ABSTRACT

Method for increasing the absorbency of cellulosic fibers by a high temperature wet treatment comprising heating the fibers in a water bath at temperatures within the range of about 95° C. to 100° C. for periods ranging from about one to sixty minutes. Absorbency of the treated fibers is thus increased by more than 2% of the corresponding untreated fibers as measured by the Syngyna Test Method. By employing such materials in catamenial tampons, sanitary napkins or the like, the amount of absorbent material may be decreased by 10% or more relative to the corresponding, untreated absorbent material, without adversely affecting the absorbent characteristics thereof.

12 Claims, No Drawings

METHOD FOR INCREASING THE ABSORBENCY OF CELLULOSIC FIBERS

BACKGROUND OF THE INVENTION

1. Field of the Invention

This invention relates to a method for improving the absorbency characteristics of cellulosic fibers, and more particularly to such a method which is useful in the preparation of absorbent materials for catamenial tampons, sanitary napkins, and other absorbent dressings.

2. Description of the Prior Art

Various techniques have been described in the literature for increasing the absorbency of cellulosic materials. Such techniques include, for example, the preparation of alloy fibers having matrices of regenerated cellulose and, uniformly dispersed therein, polyacrylates (e.g., Smith U.S. Pat. No. 3,884,287), acrylate/methacrylate copolymers (e.g., Allen et al U..S. Pat. No. 4,066,584; Meierhoefer U.S. Pat. No. 4,104,214; and Allen U.S. Pat. No. 4,240,937), alkylene vinyl ether-/ethylene dicarboxylic acid copolymers (e.g., Denning U.S. Pat. No. 4,165,743), sulfonic acids (e.g., Allen U.S. Pat. No. 4,242,242, polyvinylpyrrolidone (e.g., Smith U.S. Pat. No. 4,136,697), cellulose sulfate (e.g., Smith U.S. Pat. No. 4,273,118), carboxymethylcellulose (e.g., Smith U. S. Pat. No. 4,289,824), or the like.

Viscose rayon or other regenerated cellulose polymer alloy fibers may be subjected during preparation to one or more hot, aqueous baths. For example, post-regeneration treatments in hot water baths at temperatures of from ambient (20°–25° C.) to as much as 100° C. have been described in various of the above patents. Such treatments have not, however, been disclosed as having any appreciable effects on the absorbency characteristics of the cellulosic materials.

Other treatments of cellulosic fibrous materials have been proposed in the literature for increasing their absorbency. Thus, the treatment of carboxymethylcellulose fibers in hot aqueous baths containing cross-linking agents has been proposed to effect wet cross-linking of the fibers, with consequent increase in the absorbency thereof (see, for example, Steiger U.S. Pat. No. 3,241,553; Ells U.S. Pat. No. 3,618,607; and Chatterjee U.S. Pat. No. 3,971,379). None of this literature, however, suggests the use of hot water treatments per se for improving the absorbency of the cellulosic materials thereof.

SUMMARY OF THE INVENTION

A principal object of the present invention is to provide a new technique for treating cellulosic fibrous materials to increase the absorbency thereof. This result is obtained in accordance herewith by a high temperature wet treatment (referred to herein, for convenience, as "HTWT" processing), which comprises heating the cellulosic fibers in the presence of water at temperatures within the range of from about 95° C. to 100° C., for a period sufficient to increase the absorbency of the fibers by more than 2% of the absorbency of the corresponding untreated fibers, as measured by the well-known Syngyna Test.[1]

[1] The Syngyna Test is described, for example, in a paper entitled "A Comparison of the Absorptive Efficiency of the Commercial Catamenial Tampons", G. W. Rapp, Department of Research, Loyola University, Chicago, Ill., June 1958. The test involves the application of a radial pressure of physiological magnitude to a properly positioned tampon, while flowing a fluid having a viscosity substantially that of menstrual fluid into the tip of the tampon at a controlled rate. The absorbency of the test tampon (the grams of fluid absorbed per gram of tampon weight) is determined when the first drop of fluid begins to escape from the opposite, "string end" of the tampon material tested. The specific parameters of the Syngyna Test utilized in the work reported herein are described more fully in connection with Examples 1-9 below.

The HTWT processing hereof has been found to effect increases in absorbency of from about 2% to 16% as determined by the Syngyna Test, values which have been found to be equivalent to increased absorbencies of about 10% or greater upon actual clinical evaluation. In particular, it has been found surprisingly, that HTWT processing even imparts these increased absorbencies to regenerated cellulosic fibers which have been previously subjected to hot water processing during fiber regeneration, as well as to other cellulosic fibrous materials which have not been thus treated during manufacture.

Application of the HTWT method of the invention facilitates the saving of 10% or greater quantities of absorbent materials without substantial loss in total absorbency, as compared with similar absorbents not subjected to HTWT processing. The consequent cost economies may be quite valuable, particularly in large-scale applications such as the manufacture of tampons or sanitary napkins. Further, the HTWT method hereof may be introduced directly into conventional viscose rayon processing, to provide cellulosic fibers having improved absorbencies.

The increased absorbency obtained by HTWT processing may be attributable to morphological changes produced thereby. Thus, it is possible that the crystalline regions of the cellulosic fibers become less oriented during HTWT, increasing the cross-sectional bulk of the fibers and thereby facilitating increased water pick-up per unit area. Alternatively, it is possible that ion-exchange occurs during HTWT processing, one or more cations being extracted from the cellulose fibers during the process to yield more absorbent fibers. This mechanism may be attributable to the fact that the cellulose functional groups, CELL—OH and CELL—RCOOH, are on the fiber surfaces as a result of the tertiary molecular structure thereof. In principal, such groups can exchange hydrogen ions in aqueous solution for other cations. The precise mechanism by which HTWT processing is effective is not, however, understood as of this writing. Accordingly, it will be appreciated that the invention is not limited to either of the preceding hypotheses of to any other structural mechanism underlying the observed increases in absorbency effected by the HTWT method of the invention.

DESCRIPTION OF THE PREFERRED EMBODIMENTS

The HTWT method involves a high temperature wet treatment in the presence of water, desirably in a water bath pre-heated to and maintained within the temperature range of from about 95° C. to 100° C. On the other hand, it has been found that the increased absorbencies effected by the HTWT processing are not achieved employing either stream or dry heating of the fibers at equivalent temperatures (see Example 33 below); this result may, possibly, be attributed to the above-postulated ion-exchange mechanism which may occur only in solution. Similarly, the increased absorbencies obtained by use of the present method have not been achieved at room temperature wet treatment [RTWT] (see Controls A to H and J to L below).

The fibers are treated for a sufficient period to increase their absorbency by at least 2% as measured by the Syngyna Test. It has been found that absorbency increases of at least 2%, about up to as much as about 16%, may be achieved by carrying out the HTWT for periods varying from about one to sixty minutes.

The processing steps of the invention are preferably carried out in deionized water baths; as used herein, the term "deionized water" is intended to embrace any aqueous media in which the non-sodium metal ion concentrations have been reduced or eliminated, including distilled water, deionized water produced by ion-exchange, or the like. It has been found that the use of deionized water rather than tap water in HTWT processing imparts increased absorbency characteristics to the HTWT processed fibers (see Example 21 and Controls I and J below); the ion-exchange mechanism postulated above may account for these results.

After subjecting the cellulosic fibers to HTWT processing, they are treated with liquid water (preferably, deionized water) at ambient temperature conditions (e.g., at temperatures from about 20° C. to about 25° C.). Preferably, the cellulosic fibers are soaked in a water bath maintained at ambient conditions for periods of from about 5 to 10 minutes.

When it is desired to utilize the thus treated fibers as absorbent materials for catamenial tampons or sanitary napkins they may thereafter be dried, compressed, formed into webs (as, for example, by carding or airforming [e.g., in a "Rando Webber"]), and then formed. When, for example, it is desired to produce tampons therefrom, webs of the HTWT processed cellulosic fibers may be formed into tampons by the procedure described in Dostal, U.S. Pat. No. 3,811,445, owned by the assignee of the present invention.

The water baths (or sprays or the like) used in the method of this invention may also contain various adjuvants to impart other desired properties to the treated fibers. For example, it is preferred in the processing of cellulosic fibers to be utilized as absorbents for catamenial tampons to incorporate in the treatment baths finishing or lubricating agents such as the polyoxyethylene sorbitan monesters of higher fatty acids, e.g., polyoxyethylene sorbitan mono-laurate (AHCO 7596T, marketed by I.C.I., Industries). Other lubricating finishes, such as soaps; sulfonated oils; ethoxylated fatty acids; ethoxylated fatty esters of polyhydric alcohols; fatty acid esters combined with emulsifying agents; mixtures of the various lubricating finishes; or other conventional additives may of course also be incorporated in the water treatment baths of the invention, as desired. Desirably, such lubricating or finishing agents or other additives are incorporated in minor amounts in the treatment baths in order that the amounts of such materials deposited on the cellulosic fibers are well below 1%, and preferably within the range of from about 0.1 to 0.5%.

The improved absorbencies achieved by the present method may be determined in vitro, or in vivo in appropriately conducted clinical evaluations. For example, either the well-known Syngyna Test (see the Rapp publication referred to hereinabove, and Examples 1-9 below), or the Demand Absorbency Test (see the paper by Bernard M. Lichstein, "Demand Wettability, A New Method For Measuring Absorbency Characteristics of Fabrics", INDA Conference, March 1974, and Examples 10-19 below), may be utilized for the in vitro measurement of the absorbencies exhibited by the HTWT processed cellulosic fibers.

The techniques utilized in the HTWT processing of the invention, and the improved absorbency characteristics thus obtained, are illustrated in the following examples, wherein all temperatures are given in degrees Celsius and all parts and percentages are by weight, unless otherwise indicated.

EXAMPLES 1-9

Syngyna Testing of HTWT-Processed Cellulosic Fiber Tampons

Five 50 g. samples for a number of different test fibers were subjected to HTWT or RTWT processing, formed into tampons, and tested for absorbency (employing the Syngyna Test), as described hereinafter.

Initially, the viscose rayon (Examples 1 and 7, and Controls A and C), and the polyacrylate-rayon (Examples 2-6 and Control B) and poly(methacrylate/acrylate)-rayon (Example 8 and Control D) polymer alloy fibers were prepared by the conventional viscose process. Such a process involves converting chemical cellulose from wood pulp or cotton linters into regenerated cellulose by a series of steps in which the cellulose is first treated with a sodium hydroxide solution to mercerize it and to form alkali cellulose. The alkali cellulose, after aging, is reacted with carbon disulfide to form a soluble sodium xanthate derivative. The xanthate is thereafter dissolved in dilute aqueous sodium hydroxide to form viscose. After ripening, the viscose is spun by itself (to produce the rayon fiber) or in admixture with the material to be alloyed therewith (i.e., polyacrylic acid or a copolymer of methacrylic and acrylic acids). The viscose or viscose/alloy material mixture is thereafter spun by extrusion through a spinneret into a spin bath containing sulfuric acid and various metal salts, which coagulate the strands of the viscose-containing solution into filaments of regenerated cellulose. The regenerated fibers are each subjected to plural stretching operations, and run through an intermediate hot aqueous bath maintained at a temperature of from about 90° to 97° C. The resulting fibers, in the form of large bundles of continuous filaments or tow from the combined output of a number of spinnerets, are cut into short fibers for further treatment.

The following fibers were prepared.

| Example or Control | Fiber |
| --- | --- |
| Examples 1, 7; Controls A, C | Commercial viscose rayon staple fiber, having an average 1-9/16" fiber length, 2.85-3.15 denier, and an absorbency of 4.5-6 ml./g. of 0.85% saline solution; |
| Examples 2-6; Control B | Polyacrylate-rayon polymer alloy, prepared as described in Smith U.S. Pat. No. 3,844,287, and having an average fiber length of 1-9/16", a denier of 3.3 and an absorbency of from 7.6 to 8.1 ml./g. of the saline solution (commercially available from Avtex, Inc.) |
| Example 8; Control D | Poly(methacrylate/acrylate)-rayon polymer alloy, prepared as described in Allen et al. U.S. Pat. No. 4,066,584, and having a 1-9/16" average fiber length, a 3.3 denier, and an absorbency of 7.6-8.1 ml./g. of saline solution (commercially available from American Enka, Inc.) |

Grade B cotton fibers, containing not less than 40% of fibers 12.5 mm. or longer and not more than 20% of fibers 6.25 mm. or less in length, and retaining not less than 20 times their own weight in water, were employed as the material treated and tested in Example 9 and Control E.

The materials utilized for the preparation of the test tampons of Examples 1–6, 8 and 9, were immersed in 2000 ml. boiling water baths, the baths being brought back to a boil within one minute after immersion and thereafter, boiled for varying periods. The fiber samples were thereafter soaked for 5–30 minutes in 2000 ml. of a distilled water bath maintained at 24° C. Additionally, the water bath in examples 1,7–9, contained sufficient AHCO 7596T to leave behind 0.25% finish on the fiber.

On the other hand, the hot water bath in which the fibers employed for the test tampons of Example 7 were immersed, was maintained at 95° C.

Finally, the fibers utilized for the preparation of control tampons A, C-E were solely washed three times in 2000 ml. distilled water aliquots, the third wash (containing the appropriate level of AHCO 7596T to impart 0.25% AHCO 7596T finish on the fiber) was maintained at 24° C., without any further treatment. Control tampon B had no finish applied.

After immersion in the respective treatment baths, the various fiber samples were compressed and placed in a 65° C. forced air oven for sixteen hours for drying. The samples were then carded on a Hollingsworth card; the resulting webs were formed into cross-webbed tampons as described in the aforesaid Dostal U.S. Pat. No. 3,811,445.

The comparative absorbencies of the test and control tampons thus prepared were determined employing a syngyna device similar to that described in the noted Rapp paper. The tampons were subjected to radial pressure imposed by a prophylactic mounted within the syngyna tube and subjected to a hydrostatic pressure of either 198 mm. or 368 mm. of water (the latter being referred to herein as the "Modified Syngyna Test"). The syngyna fluid (an approximately 0.85% saline solution) was axially fed into each tampon at a rate of about 7–8 ml. per three minutes. Fluid flow was terminated, and the tampons were regarded as having reached leakage conditions, when the first drop of fluid was observed exiting from the opposite, string end of the tampon. The fluid pick-up by each tampon (the "Absorbency"), in terms of the weight of the syngyna fluid absorbed per unit weight of the tampon, was determined and compared for the various test and control tampons. The results are set forth in Table 1 below:

TABLE 1

COMPARISON OF SYNGYNA ABSORBENCY OF HTWT AND RTWT CELLULOSIC FIBER TAMPONS

| Example or Control | Process Temperature (°C.) | Process Time (min.) | Syngyna Absorbency (g/g) | % Absorbency Advantage (HTWT/RTWT) |
|---|---|---|---|---|
| Viscose Rayon Fibers | | | | |
| Ex. 1 | 100 | 5 | 4.17 | 8% |
| Control A | 24 | 5 | 3.87 | Control |
| Polyacrylate-Rayon Fibers | | | | |
| Ex. 2 | 100 | 3 | 6.26 | 10% |
| Ex. 3 | 100 | 5 | 6.36 | 12% |
| Ex. 4 | 100 | 15 | 6.04 | 6% |
| Ex. 5 | 100 | 30 | 6.47 | 14% |
| Ex. 6 | 100 | 60 | 6.23 | 9% |
| Control B | 24 | 5 | 5.69 | Control |
| Viscose Rayon Fibers | | | | |
| Ex. 7 | 95 | 2 | 4.68 | 5% |
| Control C | 24 | 2 | 4.47 | Control |
| Poly(Methacrylate/Acrylate)-Rayon Fibers | | | | |
| Ex. 8 | 100 | 5 | 5.67 | 3% |
| Control D | 24 | 5 | 5.51 | Control |
| Cotton Fibers | | | | |
| Ex. 9 | 100 | 5 | 2.95 | 16% |
| Control E | 24 | 5 | 2.54 | Control |

From the last column of Table 1 it may be seen that tampons prepared from four different cellulosic fibers and subjected to the HTWT process of the present invention exhibited syngyna absorbencies varying from 3% to 16% greater than the aborbencies of corresponding materials prepared by RTWT processing.

EXAMPLES 10–19

Demand Absorbency Testing Of HTWT-Processed Cellulosic Fiber Tampons

The relative absorbencies of additional cellulosic fiber tampons, incorporating poly (methacrylate/acrylate)-rayon alloy fiber and viscose rayon fiber absorbents, and prepared generally as described in Examples 1,7–9 above, were also determined by the Lichstein Demand Absorbency Test. In this instance, the test fibers were dried as indicated above and compressed (at pressures of at least 1000 psi) into wafers having one inch diameters and 0.15 inch thicknesses. The wafers were then placed in contact with a side fill burette containing a 0.85% aqueous saline solution, the solution being placed under a slight air pressure to initiate absorption of the solution by the respective test or control wafer. At equilibrium, the average amount of fluid absorbed (in ten determinations for each test fiber) was established in terms of the number of grams of fluid absorbed per gram of the compressed fiber, on a bone dry basis.

The ralative demand absorbency characteristics for a number of processed fibers, treated at 95° C. in accordance with the present invention or merely subjected to plural water washes at 24° C., for periods varying from one to five minutes, are given in Table 2 below:

TABLE 2

COMPARISON OF DEMAND ABSORBENCY OF HTWT AND RTWT CELLULOSIC FIBER TAMPONS

| Example or Control | Process Temperature (°C.) | Process Time (min.) | Demand Absorbency (g/g) | % Absorbency Advantage |
|---|---|---|---|---|
| Poly (Methacrylate/Acrylate)-Rayon Fibers | | | | |
| Ex. 10 | 95 | 1 | 8.14 | 3% |
| Ex. 11 | 95 | 2 | 8.43 | 7% |
| Ex. 12 | 95 | 3 | 8.40 | 6% |
| Ex. 13 | 95 | 4 | 8.34 | 6% |
| Ex. 14 | 95 | 5 | 8.31 | 5% |
| Control F | 24 | 5 | 7.89 | Control |
| Viscose Rayon Fibers | | | | |
| Ex. 15 | 95 | 1 | 6.15 | 3% |
| Ex. 16 | 95 | 2 | 6.27 | 5% |
| Ex. 17 | 95 | 3 | 6.12 | 3% |
| Ex. 18 | 95 | 4 | 6.11 | 2% |
| Ex. 19 | 95 | 5 | 6.11 | 2% |

TABLE 2-continued
COMPARISON OF DEMAND ABSORBENCY OF HTWT AND RTWT CELLULOSIC FIBER TAMPONS

| Example or Control | Process Temperature (°C.) | Process Time (min.) | Demand Absorbency (g/g) | % Absorbency Advantage |
|---|---|---|---|---|
| Control G | 24 | 5 | 5.97 | Control |

From the preceding tabulation it will be seen that the noted cellulosic fibers subjected to HTWT processing at temperatures of 95° C. and for periods as short as one minute exhibit superior absorbency characteristics, as measured by the Demand Absorbency Test, as compared with like fibers subjected to RTWT processing.

EXAMPLE 20
Clinical Test Of HTWT Rayon Tampons

Rayon test and Control H tampons (five samples each) were prepared, generally in the manner described in connection with Example 7 and Control C above. In this instance, however, in order to produce the greater quantities of material required for clinical evaluation, 100 g. of rayon fiber was placed on a sieve screen and immersed in a shaker bath containing 39 l. of distilled water maintained at 95° C. After two minutes, the fiber was removed and squeezed. After treating twelve such fiber batches in this manner, the 1200 g. of HTWT-processed fiber was soaked for three minutes in 10 l. of distilled water containig 15 g. of AHCO 7596T (which was sufficient to impart 0.25% finish on the fiber). Test tampons were prepared by compressing the fiber, drying it, carding it and forming the tampons from the resulting carded web in the manner indicated hereinabove.

Control tampons were prepared without HTWT processing, merely by soaking 1200 g. of the same rayon fiber in 10 l. of distilled water containing 15 g. of AHCO 7596T, and forming the tampons, Five samples of each of the test and control tampons thus produced were initially subjected to the Modified Syngyna Test described in connection with Examples 1–9 above and the average syngyna absorbencies were determined. In a subsequent clinical evaluation, samples of the respective test and control tampons were supplied to a test panel and quantitative absorbency data was obtained covering 49 subject periods. The average maximum absorbency of menstrual fluid prior to leakage was determined for each of the test and control tampons in the clinical study.

The clinical absorbency thus determined and the syngyna absorbency of tampons are set forth in Table 3 below:

TABLE 3
COMPARISON OF SYNGYNA AND CLINICAL ABSORBENCIES OF HTWT AND RTWT RAYON TAMPONS

| Example 20 | HTWT Tampon | RTWT Tampon (Control H) |
|---|---|---|
| A. Modified Syngyna Absorbency | | |
| Tampon Absorbency Efficiency | 3.73 g/g | 3.67 g/g |
| Absorbency Increase: | 2% | Control |
| B. Clinical Absorbency | | |
| Tampon Dry Wt. (calculated at 11% moisture): | 2.73 g | 2.81 g |
| Maximum Absorbency Prior to Leakage (g): | 8.70 g | 8.03 g |
| Clinical Absorbency Increase: | $\frac{(8.70 \text{ g} - 1) \times 100}{(8.03 \text{ g})} = 8.3\%$ | Control |
| Tampon Absorbency Efficiency: | $\frac{8.70 \text{ g}}{2.73 \text{ g}} = 3.19 \text{ g/g}$ | $\frac{8.03 \text{ g}}{2.81 \text{ g}} = 2.86 \text{ g/g}$ |
| Clinical Absorbency Efficiency Increase: | $\frac{(3.19 \text{ g} - 1) \times 100}{(2.86 \text{ g})} = 11.5\%$ | Control |

C. Tampon Weight Reduction For Absorbency Equivalence

Weight of HTWT Tampon Required for Control Tampon Total Absorbency (g.)

$$\frac{8.03 \text{ g (Total Absorbency of Control)}}{3.19 \text{ g/g (HTWT Fiber Efficiency)}} = 2.52 \text{ g (HTWT Tampon Wt.)}$$

% Decreased Weight of HTWT Tampon Required For Same Total Absorbency as Control Tampon $$\frac{(2.52 \text{ g HTWT Fiber Tampon} - 1) \times 100}{(2.81 \text{ g Control RTWT})} = -10.3\%$$

From the preceding tabulation it may be seen that the HTWT test tampons exhibited a syngyna absorbency increase relative to the RTWT control tampons of about 2%. This in vitro increase was correlated with an average increase in clinical absorbency of 8.3%, and an improved clinical absorbency efficiency of 11.5%. Finally, the calculations indicate that 10.3% less of the HTWT absorbent was required to produce the same total absorbency as th RTWT absorbent in the control tampons. The preceding experiment thus indicates that substantially lesser weights of the HTWT processed tampon material are necessary to produce the same total absorbency, as compared with conventional RTWT processed cellulosic fiber tampon materials.

To support the hypothesis that the use of a deionized water HTWT process may tend to extract cations from the processed fibers to provide greater absorbency, the treated tampon fibers of Example 20 and Control H were also analyzed for various cation contents. The results, tabulated in Table 4 below, tend to confirm that the use of a deionized water HTWT process decreases the cation contents of the processed fibers:

TABLE 4
CATIONS PRESENT IN TREATED FIBERS

| Cation | Example 20 | Control H |
|---|---|---|
| Mg | 0.03 ppm | 0.03 ppm |
| Fe | 0.01 ppm | 0.01 ppm |
| Ca | 0.35 ppm | 0.21 ppm |
| Zn | 0.02 ppm | 0.01 ppm |
| Na | 1100.0 ppm | 1400.0 ppm |
| Total Cations Analyzed | 1100.4 | 1400.3 |
| % Less Total Cation in HTWT Fiber | $\frac{1400.3 - 1100.4}{1400.4} \times 100\% = 21\%$ | |

EXAMPLE 21
Effect Of The Type Of Water Used In The HTWT Treatment On Absorbency A first group of distilled water HTWT processed tampon material (Example 21) was prepared by initially placing 30 g. of the poly(methacrylate/acrylate)-rayon fiber in a two l. glass beaker containing 1800 ml of 95° C. distilled water. After three minutes, the fibers were removed and placed in 1800 ml. of 20° C. distilled water. After three more minutes, the fibers were removed from the high temperature water bath and placed in 1000 ml. of a 45° C. distilled water bath containing 2.5 g. AHCO 7596T. After three minutes of soaking in that bath, the fibers were squeezed, dried in a 65° C. forced air oven for sixteen hours, carded and made into test tampons.

The tap water HTWT processed tampon material (Control I) was prepared in like manner save that tap water was used in each of the process solutions in lieu of distilled water.

Finally, the tap water-RTWT processed tampon material (Control J) was processed in the same manner as the tap water - HTWT processed material, except that the initial tap water treatment bath was maintained at 20° C., not 95° C.

The demand absorbency characteristics of the tap and distilled water-processed fiber tampons were determined in the same manner as described above in connection with Examples 10-19 and Controls F and G. The results are tabulated below:

TABLE 5
EFFECT OF TYPE OF WATER USED IN HTWT TREATMENT ON ABSORBENCY

| Example or Control | Water Quality | Process Time/ Temp. | Demand Absorbency (g/g) | % Absorbency Advantage Relative to Control J |
|---|---|---|---|---|
| Ex. 21 | Distilled | 3 min/95° C. | 8.16 | 7% |
| Control I | Tap | 3 min/95° C. | 7.71 | 1% |
| Control J (RTWT) | Tap | 3 min/20° C. | 7.64 | Control |

As may be seen from the preceding it was found that employing poly(methacrylate/acrylate)-rayon tampon fiber treated with deionized water at the elevated temperature exhibited absorbencies averaging some 7% greater than tampons prepared from the same material but processed in like manner at only 20° C. On the other hand, tampon fiber processed in tap water at the same elevated temperature possessed absorbencies averaging only 1% greater than the tap water-RTWT control.

EXAMPLES 22-32
Effect On Absorbency Of Drying Poly(Methacrylate/Acrylate) Rayon Alloy Fibers Prior To HTWT Processing The absorbency characteristics of poly(methacrylate/acrylate)-rayon fibers which have been dried after fiber formation (Examples 28-32), and similar fibers not subjected to drying after initial formation (Examples 22-27) were compared. The former, "dried" fibers and the later, "never dried" fibers were prepared by the same technique described in connection with Examples 1-9 above, save that only the former were dried after regeneration and prior to the subsequent HTWT processing.

The comparative absorbencies of the "dried" and "never dried" fibers subjected to HTWT processing for varying periods were determined by the Demand Absorbency test described above. As may be seen from Table 6 below, the HTWT-processed fibers each exhibited from about a 2% to 4% increase in demand absorbency relative to the corresponding fibers (Controls K and L) not subjected to HTWT processing; there was not, however, any substantial difference between the absorbency characteristics of "dried" fibers (Examples 28-32 and Control L) and those "never dried" (Examples 22-27 and Control K). It thus appears that pre-drying of the poly(methacrylate/acrylate)-rayon fiber alloy materials of these examples has no appreciable effect on fiber absorbency.

TABLE 6
EFFECT OF FIBER CONDITION ON ABSORBENCY

| Example or Control | Process Time/ Temp. | Demand Absorbency (g/g) | % Absorbency Advantage |
|---|---|---|---|
| "Never Dried" Fiber | | | |
| Ex. 22 | 1 min./100° C. | 7.78 | 2% |
| Ex. 23 | 2 min./100° C. | 7.78 | 2% |
| Ex. 24 | 3 min./100° C. | 7.81 | 3% |
| Ex. 25 | 4 min./100° C. | 7.74 | 2% |
| Ex. 26 | 5 min./100° C. | 7.76 | 2% |
| Ex. 27 | 10 min./100° C. | 7.76 | 2% |
| Control K | 5 min./24° C. | 7.61 | Control |
| "Dried" Fiber | | | |
| Ex. 28 | 1 min./100° C. | 7.82 | 0% |
| Ex. 29 | 2 min./100° C. | 7.96 | 2% |
| Ex. 30 | 3 min./100° C. | 8.13 | 4% |
| Ex. 31 | 4 min./100° C. | 8.04 | 3% |
| Ex. 32 | 5 min./100° C. | 7.96 | 2% |
| Control L | 5 min./24° C. | 7.82 | Control |

EXAMPLE 33
Effect Of Heating Method On The Absorbency Of Polyacrylate-Rayon Alloy Fibers Polyacrylate-rayon fibers were processed by the wet treatment of the present invention (Example 33), by immersion in a water bath at ambient temperature (Control M) by treatment with steam at 100° C. (Controls O, P and Q), and by treatment with dry heat at 100° C. (Controls S, T and U), tampons were produced therefrom, and the demand absorbency characteristics relative to corresponding untreated tampons of like materials (Controls N and R) were thereafter determined. The HTWT-and RTWT-processed fibers of Example 33 and Control M were prepared substantially as described in connection with Examples 2–6 and Control B above.

The demand absorbency of each of the thus processed (or unprocessed) fibers were thereafter determined; the comparative results are tabulated in Table 7 below:

TABLE 7

EFFECT OF HEATING METHOD ON ABSORBENCY

| Example or Control | Heating Method | Treatment Time | Demand Absorbency (g/g) | % Absorbency Advantage |
|---|---|---|---|---|
| Ex. 33 | HTWT(100° C.) | 3 min. | 9.29 | 9.3% |
| Control M | RTWT(20° C.) | 3 min. | 8.50 | Control |
| Control N | None | 5 min. | 8.16 | Control |
| Control O | Steam(100° C.) | 3 min. | 8.17 | — |
| Control P | Steam(100° C.) | 5 min. | 8.17 | — |
| Control Q | Steam(100° C.) | 30 min. | 8.08 | −1% |
| Control R | None | 5 min. | 8.46 | Control |
| Control S | Dry(100° C). | 3 min. | 8.17 | −3% |
| Control T | Dry(100° C). | 10 min. | 8.35 | −1% |
| Control U | Dry(100° C). | 60 min. | 8.31 | −2% |

From the preceding tabulation it will be seen that the increased absorbency obtained in connection with the method of the present invention (note for example the 9.3% absorbency increase of the tampons of Example 33, relative to the RTWT Control M), was not achieved upon processing of the like fibers with steam (Controls O, P and Q) or dry heat (Controls S, T and U) at the same temperature. The data in this experiment thus indicates that the improved absorbency obtained in accordance with the present invention is dependent on the use of wet treatment conditions, e.g., the immersion of the cellulosic fibers in a heated water bath.

In summary, the absorbency of cellulosic fibers can be substantially increased by a high temperature wet treatment comprising the heating of the fibers in a water bath at temperatures in the range of 95° C. to 100° C. for about one to sixty minutes. The resultant absorbency increase exceeds 2% of the corresponding untreated fibers as measured by the Syngyna Test. Thus, application of this HTWT process enables the reduction of 10% or more quantities of absorbent materials in the manufacture of tampons or sanitary napkins or the like as compared to the same absorbent product having untreated absorbent materials.

It should be understood that the preceding examples illustrate various embodiments of the HTWT method of the present invention, and are not intended as limiting thereof. Variations and changes which may be obvious to one skilled in the art may be made without departing from the scope and spirit of the invention which is defined in the claims appended hereto. For example, although treatment of cellulosic fibers has been preferred in the range of 95° C. to 100° C. and one to sixty minutes, these time and temperature parameters may vary depending upon the particular fiber selected for treatment.

We claim:

1. A method for increasing the absorbency of processed cotton or other processed non-regenerated cellulosic fibers, comprising:
   (a) heating, by a high temperature wet treatment, the cellulosic fibers in the presence of water at a temperature within a range of 95° C.–100° C. for a period in a range of one to sixty minutes; and
   (b) treating the fibers with water at a temperature from about 20° C. to about 25° C. for a period of from approximately 5 to 10 minutes,
   to increase the absorbency of the treated fibers by at least 2% of the absorbency of the corresponding untreated fibers as measured by the in vitro Syngyna Test Method.

2. The method of claim 1, wherein the fibers are heated in the presence of deionized water.

3. The method of claim 1, wherein the fibers are heated in the presence of a finishing or lubricating agent in an amount such that no more than 0.5% of the finish is deposited on the fibers.

4. The method of claim 3, wherein the finishing agent is a polyoxyethylene sorbitan monoester of a higher fatty acid.

5. A method of claim 1, wherein the high temperature wet treatment involves heating the fibers in a deionized water bath.

6. The method of claim 5, wherein after the high temperature wet treatment, the fibers are compressed and dried, and formed into catamenial tampons.

7. In a method for increasing the absorbency of formed viscose rayon or regenerated cellulose polymer alloy fibers, wherein a viscose or viscose polymer alloy mixture is spun by extrusion through a spinneret into a spin bath to coagulate the resulting strands of viscose or viscose polymer alloy into filaments of regenerated cellulose, and the filaments of regenerated cellulose are subjected to conventional viscose processing and converted into fibers for application, the improvement comprising:
   (a) subjecting the thus processed cellulosic fibers to an after-treatment involving heating the fibers in the presence of water at a temperature within the range of 95° C. to 100° C. for a period of from one to sixty minutes; and
   (b) treating the fibers with water at a temperature from about 20° C. to about 25° C. for a period from approximately 5 to 10 minutes,
   to increase the absorbency of the treated fibers by at least 2% of their original absorbency as measured by the in vitro Syngyna Test Method.

8. The method of claim 7, wherein the fibers are selected from the group consisting of rayon, polyacrylate-rayon and poly(acrylate/methacrylate)-rayon polymer alloy fibers.

9. The method according to claim 7, in which the after-treatment comprises heating the fibers in the presence of deionized water.

10. The method of claim 7, in which the after-treatment comprises heating the fibers in the presence of a finishing or lubricating agent in an amount such that no more than 0.5% of the finish is deposited on the fibers.

11. The method of claim 10, wherein the finishing agent is a polyoxyethylene sorbitan monoester of a higher fatty acid.

12. The method of claim 7, wherein after the high temperature wet treatment, the fibers are compressed and dried, and formed into catamenial tampons.

* * * * *